(12) United States Patent
Knippels et al.

(10) Patent No.: US 11,389,492 B2
(45) Date of Patent: Jul. 19, 2022

(54) METHOD FOR INDUCING ORAL TOLERANCE VIA ADMINISTRATION OF BETA-LACTOGLOBULIN DERIVED PEPTIDES IN COMBINATION WITH PROBIOTIC

(71) Applicant: N.V. Nutricia, Zoetermeer (NL)

(72) Inventors: Leon Matthieu Johannes Knippels, Utrecht (NL); Johan Garssen, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 0 days.

(21) Appl. No.: 15/558,669

(22) PCT Filed: Mar. 17, 2016

(86) PCT No.: PCT/NL2016/050190
§ 371 (c)(1),
(2) Date: Sep. 15, 2017

(87) PCT Pub. No.: WO2016/148572
PCT Pub. Date: Sep. 22, 2016

(65) Prior Publication Data
US 2018/0110811 A1    Apr. 26, 2018

(30) Foreign Application Priority Data
Mar. 18, 2015    (NL) ................. PCT/NL2015/050173

(51) Int. Cl.
| | |
|---|---|
| *A01N 63/00* | (2020.01) |
| *A61K 35/745* | (2015.01) |
| *A61K 38/17* | (2006.01) |
| *A23L 33/00* | (2016.01) |
| *A23L 33/18* | (2016.01) |
| *A23L 33/19* | (2016.01) |
| *A61K 35/744* | (2015.01) |
| *A61K 38/01* | (2006.01) |
| *A61K 45/06* | (2006.01) |
| *A23L 33/135* | (2016.01) |
| *A61P 37/08* | (2006.01) |
| *A61K 31/702* | (2006.01) |

(52) U.S. Cl.
CPC .......... *A61K 35/745* (2013.01); *A23L 33/135* (2016.08); *A23L 33/18* (2016.08); *A23L 33/19* (2016.08); *A23L 33/30* (2016.08); *A23L 33/40* (2016.08); *A61K 31/702* (2013.01); *A61K 35/744* (2013.01); *A61K 38/018* (2013.01); *A61K 38/1722* (2013.01); *A61K 45/06* (2013.01); *A61P 37/08* (2018.01); *A23V 2002/00* (2013.01); *A23Y 2300/29* (2013.01); *A23Y 2300/55* (2013.01)

(58) Field of Classification Search
USPC ..................................... 424/93, 400
See application file for complete search history.

(56) References Cited

U.S. PATENT DOCUMENTS

| | | | |
|---|---|---|---|
| 2009/0297545 A1 | 12/2009 | Gauthier et al. | |
| 2010/0158882 A1* | 6/2010 | Zuurendonk | ........ A23C 9/1234 424/93.45 |
| 2014/0335129 A1* | 11/2014 | Knippels | ............. A61K 31/733 424/276.1 |

FOREIGN PATENT DOCUMENTS

| | | | |
|---|---|---|---|
| AU | 2013407963 B2 * | 10/2019 | ............. A23L 33/40 |
| EP | 1 364 586 A1 | 11/2003 | |
| EP | 2 436 389 A1 | 4/2012 | |
| JP | 2008-195618 A | 8/2008 | |
| KR | 2014/0030354 A | 3/2014 | |
| WO | WO-02/24883 A2 | 3/2002 | |
| WO | WO-2011/151060 A1 | 12/2011 | |
| WO | WO-2013/083691 A1 | 6/2013 | |

OTHER PUBLICATIONS

Prescott et al. Journal of Allergy and Immunology , vol. 120, issue 2, pp. 255-262, 2007 (Year: 2007).*
Prioult et al. Clinical and Diagnostic Laboratory Bacteriology vol. 10, No. 5, pp. 787-792 , Sep. 2003 (Year: 2003).*
Guenolee et al., "Stimulation of interleukin-10 production by acidic beta-lactoglobulin-derived peptides hydrolyzed with lactobacillus paracasei NCC2461 peptidases", Clinical and Diagnostic Laboratory Immunology, Mar. 2004, vol. 11, No. 2, pp. 266-271.
International Search Report issued in International Patent Application No. PCT/NL2016/050190, dated Jul. 18, 2016.

* cited by examiner

*Primary Examiner* — Jana A Hines
*Assistant Examiner* — Khatol S Shahnan Shah
(74) *Attorney, Agent, or Firm* — Foley & Lardner LLP

(57) ABSTRACT

The invention pertains to the use of a probiotic and a beta-lactoglobulin-derived peptide in the manufacture of a product for use in inducing oral tolerance, and/or treatment, prevention or reducing the risk of allergy in a subject, in particular cow's milk protein allergy.

12 Claims, 6 Drawing Sheets
Specification includes a Sequence Listing.

SEQUENCE LISTING

```
<160> NUMBER OF SEQ ID NOS: 5

<210> SEQ ID NO 1
<211> LENGTH: 162
<212> TYPE: PRT
<213> ORGANISM: Bos taurus

<400> SEQUENCE: 1

Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
            20                  25                  30

Asp Ala Gln Ser Ala Pro Leu Arg Val Tyr Val Glu Glu Leu Lys Pro
        35                  40                  45
```

```
Thr Pro Glu Gly Asp Leu Glu Ile Leu Leu Gln Lys Trp Glu Asn Gly
     50                  55                  60

Glu Cys Ala Gln Lys Lys Ile Ile Ala Glu Lys Thr Lys Ile Pro Ala
 65                  70                  75                  80

Val Phe Lys Ile Asp Ala Leu Asn Glu Asn Lys Val Leu Val Leu Asp
                 85                  90                  95

Thr Asp Tyr Lys Lys Tyr Leu Leu Phe Cys Met Glu Asn Ser Ala Glu
            100                 105                 110

Pro Glu Gln Ser Leu Ala Cys Gln Cys Leu Val Arg Thr Pro Glu Val
                115                 120                 125

Asp Asp Glu Ala Leu Glu Lys Phe Asp Lys Ala Leu Lys Ala Leu Pro
    130                 135                 140

Met His Ile Arg Leu Ser Phe Asn Pro Thr Gln Leu Glu Glu Gln Cys
145                 150                 155                 160

His Ile

<210> SEQ ID NO 2
<211> LENGTH: 18
<212> TYPE: PRT
<213> ORGANISM: Artificial
<220> FEATURE:
<223> OTHER INFORMATION: peptide derived from cow's milk
      beta-lactoglobulin

<400> SEQUENCE: 2

Gln Lys Val Ala Gly Thr Trp Tyr Ser Leu Ala Met Ala Ala Ser Asp
 1               5                  10                  15

Ile Ser

<210> SEQ ID NO 3
<211> LENGTH: 18
<212> TYPE: PRT
<213> ORGANISM: Artificial
<220> FEATURE:
<223> OTHER INFORMATION: peptide derived from cow's milk
      beta-lactoglobulin

<400> SEQUENCE: 3

Trp Tyr Ser Leu Ala Met Ala Ala Ser Asp Ile Ser Leu Leu Asp Ala
 1               5                  10                  15

Gln Ser

<210> SEQ ID NO 4
<211> LENGTH: 18
<212> TYPE: PRT
<213> ORGANISM: artificial
<220> FEATURE:
<223> OTHER INFORMATION: peptide derived from cow's milk
      beta-lactoglobulin

<400> SEQUENCE: 4

Ala Ala Ser Asp Ile Ser Leu Leu Asp Ala Gln Ser Ala Pro Leu Arg
 1               5                  10                  15

Val Tyr

<210> SEQ ID NO 5
<211> LENGTH: 18
<212> TYPE: PRT
<213> ORGANISM: artificial
<220> FEATURE:
<223> OTHER INFORMATION: peptide derived from cow's milk
      beta-lactoglobulin
```

```
<400> SEQUENCE: 5

Leu Leu Asp Ala Gln Ser Ala Pro Leu Arg Val Tyr Val Glu Glu Leu
1               5                   10                  15

Lys Pro
```

METHOD FOR INDUCING ORAL TOLERANCE VIA ADMINISTRATION OF BETA-LACTOGLOBULIN DERIVED PEPTIDES IN COMBINATION WITH PROBIOTIC

CROSS-REFERENCE TO RELATED APPLICATIONS

This application is the National Phase of International Patent Application No. PCT/NL2016/050190, filed Mar. 17, 2016, published on Sep. 22, 2016 as WO 2016/148572 A1, which claims priority to International Patent Application No. PCT/NL2015/050173, filed Mar. 18, 2015. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Sep. 12, 2017, is named 069818-3040Sequencelisting.txt and is 4 KB.

The invention is in the field of immunology and more particularly relates to compositions for use in inducing oral tolerance and/or for use in treatment and/or prevention (including reducing the risk of occurrence) of allergy, in particular cow's milk protein allergy. The invention rests particularly in the field of infants and children.

BACKGROUND

One of the most common food allergies, especially in infancy and childhood, is cow's milk allergy (CMA). Dietary proteins are presented to the immune system via the gastrointestinal tract and the normal response would be to elicit a tolerogenic immune response to the ingested nutrients. This response is called oral immune tolerance or oral tolerance. The induction of oral immune tolerance is especially relevant for infants, who after birth are exposed for the first time to dietary proteins and have to adapt to this. If oral immune tolerance in infants is not established, food allergy will occur.

About 2 to 3% of infants are allergic to cow's milk protein. For infants suffering from allergy to cow's milk protein, infant formulae are on the market comprising extensively hydrolysed proteins (extensive protein hydrolysate) or even merely free amino acids as nitrogen source. In these formulae no allergenic proteins or peptides are present. Thereby exposure to milk protein is avoided thus preventing a clinically manifested allergic reaction. This is called a secondary prevention of cows' milk allergy. However, as soon as cow's milk proteins are reintroduced into the diet, the infant may again suffer from clinically manifested allergic reactions.

Hypoallergenic formulae are on the market, comprising a partial protein hydrolysate (partially hydrolysed proteins), which have a decreased allergenicity. These formulations have the advantage that they increase the likelihood of obtaining an immunological tolerogenic response to cow's milk protein or peptides, with the advantage that later on the native protein can be introduced in the diet with a reduced risk of allergic reactions. This is called primary prevention of cow's milk protein allergy and these formulae are typically used for infants at risk of developing allergy.

SUMMARY OF THE INVENTION

The inventors found that a composition comprising a probiotic and a beta-lactoglobulin-derived peptide comprising an amino acid sequence corresponding to at least 8 consecutive amino acids of the beta-lactoglobulin protein represented by SEQ ID No. 1 was surprisingly effective in inducing oral tolerance and/or for use and in treatment and/or prevention (including reducing the risk of occurrence) of allergy, suitably food allergy, in particular cow's milk protein allergy (CMA). Suitably, the composition further comprises a prebiotic.

The present invention thus concerns a method for inducing oral tolerance and/or treatment, prevention and/or reducing the risk of occurrence of allergy in a subject, comprising administering to the subject a composition comprising a probiotic and a beta-lactoglobulin-derived peptide comprising an amino acid sequence corresponding to at least 8 consecutive amino acids of the beta-lactoglobulin protein represented by SEQ ID No. 1. Suitably, the composition further comprises a prebiotic. In one embodiment, the method is for inducing oral tolerance. In one embodiment, the method is for treatment and/or prevention of allergy, suitably food allergy, more suitably CMA.

The invention may also be worded as the use of a probiotic and a beta-lactoglobulin-derived peptide comprising an amino acid sequence corresponding to at least 8 consecutive amino acids of the beta-lactoglobulin protein represented by SEQ ID No. 1 for the manufacture of a composition for inducing oral tolerance and/or treatment, prevention and/or reducing the risk of occurrence of allergy in a subject. Suitably, the composition further comprises a prebiotic. In one embodiment, the use is for the manufacture of a composition for inducing oral tolerance. In one embodiment, the use is for the manufacture of a composition for treatment and/or prevention of allergy, suitably food allergy, more suitably CMA.

In other words, the invention concerns a composition for use in inducing oral tolerance and/or treatment, prevention and/or reducing the risk of occurrence of allergy in a subject, said composition comprising a probiotic and a beta-lactoglobulin-derived peptide comprising an amino acid sequence corresponding to at least 8 consecutive amino acids of the beta-lactoglobulin protein represented by SEQ ID No. 1. The composition suitably further comprises a prebiotic. Worded differently, the invention pertains to a composition comprising a probiotic and a beta-lactoglobulin-derived peptide for use in oral tolerance, and/or treatment, prevention or reducing the risk of allergy in a subject, said peptide comprising an amino acid sequence corresponding to at least 8 consecutive amino acids of the beta-lactoglobulin protein represented by SEQ ID No. 1. Suitably, the composition further comprises a prebiotic. In one embodiment, the use is for inducing oral tolerance. In one embodiment, the use is for treatment and/or prevention of allergy, suitably food allergy, more suitably CMA.

The invention also concerns a composition comprising a probiotic and a beta-lactoglobulin-derived peptide comprising an amino acid sequence corresponding to at least 8 consecutive amino acids of the beta-lactoglobulin protein represented by SEQ ID No. 1.

The invention also concerns a kit-of-parts comprising a first container comprising infant nutrition and a second container comprising a beta-lactoglobulin-derived peptide comprising an amino acid sequence corresponding to at least 8 consecutive amino acids of the beta-lactoglobulin protein represented by SEQ ID No. 1, wherein the infant nutrition comprises a probiotic or wherein the kit-of-parts comprises a third container comprising a probiotic.

In one embodiment of the method, use, composition for use or composition according to the invention, the beta-lactoglobulin-derived peptide comprises an amino acid sequence consisting of 12-30 consecutive amino acids from the region spanning from amino acids 13 to 48 of the beta-lactoglobulin protein represented by SEQ ID No. 1. In one embodiment of the method, use, composition for use or composition according to the invention, the beta-lactoglobulin-derived peptide consists of an amino acid sequence selected from the group consisting of SEQ ID No. 2, SEQ ID No. 3, SEQ ID No. 4 and SEQ ID No. 5, optionally coupled to 1-6 further amino acids at its C- and/or N-terminus. In one embodiment of the method, use, composition for use or composition according to the invention, the composition further comprises a prebiotic. In one embodiment of the method, use, composition for use or composition according to the invention, the prebiotic is selected from the group consisting of fructo-oligosaccharide, non-digestible dextrin, galacto-oligosaccharide, xylo-oligosaccharide, arabino-oligosaccharide, arabino-galacto-oligosaccharide, gluco-oligosaccharide, glucomanno-oligosaccharide, galactomanno-oligosaccharide, mannan-oligosaccharide, chito-oligosaccharide, uronic acid oligosaccharide, sialyl-oligosaccharide and fuco-oligosaccharide. In one embodiment of the method, use, composition for use or composition according to the invention, the prebiotic comprises a mixture of a short-chain oligosaccharide having an average degree of polymerisation of 2-8 and a long-chain oligosaccharide having an average degree of polymerisation of 10-60. In one embodiment of the method, use, composition for use or composition according to the invention, the prebiotic comprises a galacto-oligosaccharide and/or a fructo-oligosaccharide. In one embodiment of the method, use, composition for use or composition according to the invention, the probiotic comprises a strain of the genus *Bifidobacteria, Lactobacillus,* or *Streptococcus.* In one embodiment of the method, use, composition for use or composition according to the invention, the probiotic comprises a strain selected from the group consisting of *Bifidobacterium breve, Bifidobacterium longum, Bifidobacterium infantis, Bifidobacterium bifidum, Lactobacillus acidophilus, Lactobacillus paracasei, Lactobacillus johnsonii, Lactobacillus plantarum, Lactobacillus reuteri, Lactobacillus rhamnosus, Lactobacillus casei, Lactobacillus lactis* and *Streptococcus thermophiles.* In one embodiment of the method, use, composition for use or composition according to the invention, the probiotic comprises *Bifidobacterium breve* and/or *Bifidobacterium longum.* In one embodiment of the method, use, composition for use or composition according to the invention, the composition comprises 10-5000 µg beta-lactoglobulin-derived peptides per gram total protein. In one embodiment of the method, use or composition for use according to the invention, the allergy is cow's milk protein allergy.

DETAILED DESCRIPTION

The present invention concerns a method for inducing oral tolerance and/or treatment and/or prevention of allergy in a subject, wherein the method involves administration of a composition to said subject, said composition comprising a probiotic and a beta-lactoglobulin-derived peptide comprising an amino acid sequence corresponding to at least 8 consecutive amino acids of the beta-lactoglobulin protein represented by SEQ ID No. 1.

In the experiments, mice had been sensitized to intact whey protein and consequently showed an acute allergic skin response after an intradermal challenge with intact whey protein, i.e. they had become whey protein allergic, which was also proven by an increase in whey-specific IgE (data not shown). The inventors surprisingly found that the allergic reaction to whey protein upon further administration of whey protein was significantly suppressed (or reduced) when the composition of the invention was administrated prior to the whey protein challenge. In other words, administration of the composition according to the invention induced oral tolerance.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

In the context of the present invention, reference is made to the following amino acid sequences:

| SEQ ID | Sequence |
|---|---|
| No. 1 | L I V T Q T M K G L D I Q K V A G T W Y S L A M A A S D I S L L D A Q S A P L R V Y V E E L K P T P E G D L E I L L Q K W E N G E C A Q K K I I A E K T K I P A V F K I D A L N E N K V L V L D T D Y K K Y L L F C M E N S A E P E Q S L A C Q C L V R T P E V D D E A L E K F D K A L K A L P M H I R L S F N P T Q L E E Q C H I |
| No. 2 | Q K V A G T W Y S L A M A A S D I S |
| No. 3 | W Y S L A M A A S D I S L L D A Q S |
| No. 4 | A A S D I S L L D A Q S A P L R V Y |
| No. 5 | L L D A Q S A P L R V Y V E E L K P |

Composition

In a first aspect, the invention concerns a composition comprising a probiotic and a beta-lactoglobulin-derived peptide comprising an amino acid sequence corresponding to at least 8 consecutive amino acids of the beta-lactoglobulin protein represented by SEQ ID No. 1. The composition according to the invention is to be used in the method or use or composition for use according to the invention, which involve administration of the composition according to the invention. The composition according to the invention may be used as a pharmaceutical product or a nutritional product.

The probiotic and the beta-lactoglobulin-derived peptide, and suitably the prebiotic, are present in therapeutically effective amounts.

In one aspect, the composition according to the invention may be used as a pharmaceutical product comprising one or more pharmaceutically acceptable carrier materials. Such product may contain the daily dosages as defined below in one or more dosage units. The dosage unit may be in a liquid form or in a solid form, wherein in the latter case the daily dosage may be provided by one or more solid dosage units, e.g. in one or more capsules or tablets. The pharmaceutical product, suitably for enteral application, may be a solid or liquid galenical formulation. Examples of solid galenical formulations are tablets, capsules (e.g. hard or soft shell gelatine capsules), pills, sachets, powders, granules and the like which contain the active ingredients together with conventional galenical carriers. Any conventional carrier material can be utilized. The carrier material can be organic or inorganic inert carrier material suitable for oral administration. Suitable carriers include water, gelatine, gum arabic, lactose, starch, magnesium stearate, talc, vegetable oils, and the like. Additionally, additives such as flavouring agents, preservatives, stabilizers, emulsifying agents, buffers and the like may be added in accordance with accepted practices of pharmaceutical compounding. While the individual active ingredients are suitably administered in a single composition, they may also be administered in individual dosage units.

In one aspect, the composition according to the invention may be used as a nutritional product, for example as a nutritional supplement, e.g. as an additive to a normal diet, as a fortifier, to add to a normal diet, as a complete nutrition or as infant nutrition suitable for feeding infants (e.g. infant formula or follow-on formula). The nutritional product suitably comprises fats, proteins, and carbohydrates. It is understood that a nutritional product differs from a pharmaceutical product by the presence of nutrients which provide nutrition to the subject to which the composition is administered, for instance the presence of protein, fat, digestible carbohydrates and dietary fibres. It may further contain ingredients such as minerals, vitamins, organic acids, and flavouring agents. Although the term "nutraceutical product" is often used in literature, it denotes a nutritional product with a pharmaceutical component or pharmaceutical purpose. Hence, the nutritional composition according to the invention may also be used in a nutraceutical product.

The composition of the invention is typically an enteral composition, i.e. intended for oral administration. It is suitably administered in liquid form. For instance, the composition may comprise water in which the further components are dissolved or suspended. The composition is thus suitably a liquid, or a solid (typically a powder or tablet) which is reconstitutable with a liquid, suitably with water, to obtain a liquid composition. Suitably the liquid composition has a viscosity below 100 mPa·s, more suitably below 60 mPa·s, more suitably below 35 mPa·s, even more suitably below 6 mPa·s as measured in a Brookfield viscometer at 20° C. at a shear rate of 100 $s^{-1}$.

The composition typically comprises a lipid fraction, a protein component and a digestible carbohydrate component. The caloric content of the composition, when in liquid form, suitably comprises 60 to 85, more suitably 60 to 70 kcal/100 ml liquid. The osmolarity of the present composition is suitably between 150 and 420 mOsmol/l, more suitably 260 to 360 mOsmol/l.

Suitably the lipid component provides 2.9 to 6 g lipid per 100 kcal, suitably the protein component provides 1.8 to 5.5 g per 100 kcal, suitably 1.8 to 2.5 g per 100 kcal and suitably the digestible carbohydrate component provides 9 to 14 g per 100 kcal, of the composition. The amount of total calories is determined by the sum of calories derived from protein, lipids, digestible carbohydrates and non digestible oligosaccharides.

Protein

The composition according to the invention comprises a protein fraction, which at least includes the aforementioned beta-lactoglobulin-derived peptide. Beta-lactoglobulin is one of two major whey proteins in the milk of cows and sheep but is not found in human milks. Often in case of cow's milk protein allergy beta-lactoglobulin is the allergen.

The beta-lactoglobulin-derived peptide according to the invention is a peptide comprising an amino acid sequence corresponding to at least 8, suitably 10-50 amino acids, more suitably 12-30, more suitably 14-25, more suitably 16-20, most suitably 18 consecutive amino acids of the beta-lactoglobulin protein represented by SEQ ID No. 1.

In the context of the invention, an amino acid sequence "corresponding to" the beta-lactoglobulin protein allows for at most three, more suitably at most two, even more suitably one amino acid substitution in the amino acid sequence may be allowed for, said substitution(s) suitably being conservative amino acid substitution(s). A "conservative amino acid substitution" refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Suitable conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Suitably, the amino acid change is conservative. Suitable conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu. In particular, the Glu (E) to Gln (Q) substitution of amino acid 45 within SEQ ID No. 1 is covered by the present invention. SEQ ID No. 1 represents the B variant of the beta-lactoglobulin protein, while Glu to Gln substitution at amino acid 45 gives the D variant, which are both suitably used in the context of the present invention. In one embodiment, no modifications including conservative amino acid substitutions other than the Glu to Gln substitution of amino acid 45 within the suitable amino acid sequence regions of SEQ ID No. 1 is allowed for. In one embodiment, no modifications including conservative amino acid substitutions in the suitable amino acid sequence regions is allowed for.

Suitably, the amino acid sequence contains consecutive amino acids from the region spanning from amino acids 3 to 117, more suitably amino acids 10 to 63, most suitably amino acids 13 to 48, of the beta-lactoglobulin protein.

Suitably, the peptide has a molecular weight of at most 5 kDa, in particular from 0.1 to 4.9 kDa, suitably from 0.5 to 4.5, more suitably of 2 to 4 kDa, most suitably of about 2.4 kDa. In a suitable embodiment the beta-lactoglobulin-derived peptide consists of 12 to 30 amino acids, suitably 14 to 25 amino acids, more suitably 16 to 20 amino acids, most suitably 18 amino acids. Suitable beta-lactoglobulin-derived peptides comprise, most suitably consist of, the amino acid sequences represented by SEQ ID No. 2 (amino acids 13 to 30 of SEQ ID No. 1), SEQ ID No. 3 (amino acids 19 to 36 of SEQ ID No. 1), SEQ ID No. 4 (amino acids 25 to 42 of SEQ ID No. 1) and SEQ ID No. 5 (amino acids 31 to 48 of SEQ ID No. 1), wherein amino acid 15 in SEQ ID No. 5 (corresponding to amino acid 45 in SEQ ID No. 1) may be substituted with Gln (Q).

The beta-lactoglobulin-derived peptide may comprise further amino acids at the C- and/or N-terminus of the amino acid sequence corresponding to at least 8 consecutive amino acids of the beta-lactoglobulin protein. In other words, the amino acid sequence corresponding to at least 8 consecutive amino acids of the beta-lactoglobulin protein is optionally coupled to further amino acids at its C- and/or N-terminus. Typically, 1-6 further amino acids may be present, suitably 1-5, more suitably 1-4, most suitably 1-3 further amino acids may be present, which can be any (combination of) amino acid(s). In one embodiment, no further amino acids are present at the C- and/or N-terminus of the at least 8 consecutive amino acids of the beta-lactoglobulin protein. Suitably, the beta-lactoglobulin-derived peptide consists of an amino acid sequence selected from the group consisting of SEQ ID No. 2, SEQ ID No. 3, SEQ ID No. 4, SEQ ID No. 5 and SEQ ID No. 5 wherein amino acid 15 is substituted with Gln (Q). Most suitably, the beta-lactoglobulin-derived peptide consists of an amino acid sequence selected from the group consisting of SEQ ID No. 2, SEQ ID No. 3, SEQ ID No. 4 and SEQ ID No. 5.

The composition may comprise more than one distinct beta-lactoglobulin-derived peptide, such as 2, 3, 4, 5 or even more, e.g. up to 2 or up to 10, distinct beta-lactoglobulin-derived peptides. Suitably, the composition comprises 1-10 distinct beta-lactoglobulin-derived peptides, more suitably 2-5 distinct beta-lactoglobulin-derived peptides, most suitably 4 distinct beta-lactoglobulin-derived peptides. Herein, each distinct beta-lactoglobulin-derived peptide comprises a different amino acid sequence of the beta-lactoglobulin protein represented by SEQ ID No. 1. The difference may reside in the number of amino acids from the beta-lactoglobulin protein sequence and/or in the location of the amino acid sequence within the beta-lactoglobulin protein sequence, suitably it resides in the location of the amino acid sequence within the beta-lactoglobulin protein.

The mixture of more than one distinct beta-lactoglobulin-derived peptide suitably comprises at least one, more suitably 2-4, even more suitably 3 or 4, most suitably all 4, beta-lactoglobulin-derived peptide(s) consisting of an amino acid sequence selected from the group consisting of SEQ ID No. 2, SEQ ID No. 3, SEQ ID No. 4 and SEQ ID No. 5.

In accordance with the present invention, the beta-lactoglobulin-derived peptides can be chemically synthesised as known in the art, or isolated after expression by a genetically modified host such as an *E. Coli* strain or *Lactobacillus* strain. Alternatively the peptides are isolated and purified from a whey protein or beta-lactoglobulin hydrolysate.

The composition according to the invention may comprise further proteinaceous material, in addition to the beta-lactoglobulin-derived peptide(s), although the beta-lactoglobulin-derived peptide(s) may also be the only protein source. In the context of the present invention the additional "protein" or "proteinaceous material" encompasses proteins, peptides, free amino acids and partially or extensively hydrolysed proteins. Typically, extensive protein hydrolysates have a free amino acid content of above 10 g per 100 g protein. Any additional extensively hydrolysed protein in the present invention suitably relates to protein which has been hydrolysed and has less than 3 wt % of peptides with a size above 5 kDa. Typically, extensively hydrolysed protein has been obtained by protease hydrolysis followed by an ultrafiltration step by filtrating over a membrane with a cut-off of 2-5 kDa. Suitably these extensive protein hydrolysates comprise almost no peptides with a size over 1.5 kDa.

Suitably, the further proteinaceous material—additional to the beta-lactoglobulin-derived peptide—does not evoke an allergic reaction, such as free amino acids, partially hydrolysed protein and/or extensively hydrolysed protein. As a further protein component, i.e. apart from the beta-lactoglobulin-derived peptide, the composition according to the present invention suitably comprises free amino acids, partially hydrolysed whey protein and/or extensively hydrolyzed whey proteins.

In some embodiments, the composition according to the present invention does not contain intact cow's milk protein. The composition may comprise an additional protein component selected from the group consisting of free amino acids, extensively hydrolysed whey protein and proteins from other sources such as soy, pea, rice, collagen or the like, in intact form, in partially hydrolysed form, and/or in extensively hydrolysed form.

The present composition suitably contains at least 50 wt % protein component derived from non-human milk, more suitably at least 90 wt %, based on dry weight of total protein.

The present composition suitably contains 4 to 25%, more suitably 5 to 20%, more suitably 7 to 16%, most suitably 7 to 12% protein, based on total calories. The present composition, when in liquid form, suitably contains 0.5 to 6.0 g, more suitably 0.8 to 3.0 g, even more suitably 1.0 to 2.5 g of protein per 100 ml. The present composition suitably comprises at least 7.0 wt %, more suitably at least 8.0 wt %, most suitably at least 9 or at least 10 wt % protein based on dry weight of the total composition. Suitably, the present composition comprises at most 40 wt %, more suitably at most 15 wt %, suitably at most 20 wt % of protein based on dry weight of the total composition.

In a suitable embodiment of the present invention, the present composition comprises at least 10 μg, more suitably at least 30 μg, suitably at least 50 μg, suitably 10 to 5000 μg, more suitably 20 to 2000 μg, more suitable 30 to 500 μg and particularly suitably 50 to 250 μg of the beta-lactoglobulin-derived peptide per gram of total protein.

Carbohydrate

The composition according to the invention may comprise a carbohydrate fraction, which may include a prebiotic. In the context of the present invention, the term "prebiotic" refers to one or more non-digestible oligosaccharides. Advantageously, the non-digestible oligosaccharide is water-soluble (according to the method disclosed in L. Prosky et al, J. Assoc. Anal. Chem 71: 1017-1023, 1988). Non-digestible oligosaccharides are not digested in the intestine by the action of digestive enzymes present in the human upper digestive tract (small intestine and stomach) but instead are fermented by the human intestinal microbiota.

Suitable non-digestible oligosaccharides are selected from the group consisting of fructo-oligosaccharide, non-digestible dextrin, galacto-oligosaccharide, xylo-oligosaccharide, arabino-oligosaccharide, arabinogalactooligosaccharide, gluco-oligosaccharide, glucomannooligosaccharide, galactomanno-oligosaccharide, mannanoligosaccharide, chito-oligosaccharide, uronic acid oligosaccharide, sialyl-oligosaccharide and fuco-oligosaccharide. Especially suitable non-digestible oligosacchardies are fructo-oligosaccharides and/or galacto-oligosaccharides. The oligosaccharides suitably have a degree of polymerization of 2-200. In one embodiment, fructo-oligosaccharides and fructo-polysaccharides (and mixtures thereof) with a DP of 2-200 are suitable prebiotics in the context of the invention.

One suitable type of oligosaccharide is a short-chain oligosaccharide which has an average degree of polymerisation of less than 10, suitably at most 8, suitably in the range of 2-7. The short-chain oligosaccharide suitably comprises galacto-oligosaccharides and/or fructo-oligosaccharides. In one embodiment, the composition comprises galacto-oligosaccharides, in particular β-galacto-oligosaccharides, more in particular trans-galacto-oligosaccharides. The galacto-oligosaccharides suitably have an average degree of polymerisation in the range of 2-8, i.e. are short-chain oligosaccharides in the context of the invention.

Suitably, the composition comprises short-chain fructo-oligosaccharides and/or short-chain galacto-oligosaccharides, suitably at least short-chain fructo-oligosaccharides. (trans)galactooligosaccharide is for example available under the trade name Vivinal® GOS (Borculo Domo Ingredients, Zwolle, Netherlands), Bimuno (Clasado), Cup-oligo (Nissin Sugar) and Oligomate55 (Yakult). Fructooligosaccharides may be inulin hydrolysate products having an average DP within the aforementioned (sub-) ranges; such FOS products are for instance commercially available as Raftilose P95 (Orafti) or with Cosucra.

Another suitable type of oligosaccharide is long-chain fructo-oligosaccharides which has an average degree of polymerisation above 10, typically in the range of 10-100, suitably 15-50, most suitably above 20. A particular type of long-chain fructo-oligosaccharides is inulin, such as Raftilin HP.

The present composition may contain one type of non-digestible oligosaccharide or a mixture of two or more types of non-digestible oligosaccharides, suitably it comprises a mixture of two or more non-digestible oligosaccharides, most suitably a mixture of two non-digestible oligosaccharides. In case the prebiotic contains or consists of a mixture of two distinct oligosaccharides, one oligosaccharide may be short-chain as defined above and one oligosaccharide may be long-chain as defined above. Suitably, short-chain oligosaccharides and long-chain oligosaccharides are present in a weight ratio short-chain to long-chain in the range of 1:99-99:1, more suitably 1:1-99:1, more suitably 4:1-97:3, even more suitably 5:1-95:5, even more suitably 7:1-95:5, even more suitably 8:1-10:1, most suitably about 9:1.

In one embodiment, the prebiotic comprises a mixture of fructo-oligosaccharides and/or galacto-oligosaccharides. Suitable mixtures include mixtures of long-chain fructo-oligosaccharides with short-chain fructo-oligosaccharides or short-chain galacto-oligosaccharides, most suitably long-chain fructo-oligosaccharides with short-chain fructo-oligosaccharides.

In one embodiment, the prebiotic comprises a mixture of fructo-oligosaccharides, most suitably a mixture of short-chain fructo-oligosaccharides (sc-FOS) and long-chain fructo-oligosaccharides (lc-FOS). These fructo-oligosaccharides suitably account for at least 80 wt %, more suitably at least 90 wt % of the prebiotic. In a most suitable embodiment, the prebotic fraction consists of a mixture of sc- and lc-FOS.

The prebiotics may be present in the composition at any suitable concentration, suitably. The present composition suitably comprises 0.05 to 20 wt % of said non-digestible oligosaccharides, more suitably 0.5 to 15 wt %, even more suitably 1 to 10 wt %, most suitably 2 to 10 wt %, based on dry weight of the present composition. When in liquid form, the present composition suitably comprises 0.01 to 2.5 wt % non-digestible oligosaccharide, more suitably 0.05 to 1.5 wt %, even more suitably 0.25 to 1.5 wt %, based on 100 ml.

The composition according to the invention may comprise further carbohydrates, suitably the present composition comprises a digestible carbohydrate. Typically, digestible carbohydrates that are known in the art to be suitable for use in infant nutritional compositions are used. Suitably, the digestible carbohydrate is selected from digestible polysaccharides (e.g. starch, matodextrin), digestible monosaccharides (e.g. glucose, fructose), and digestible disaccharides (e.g. lactose, sucrose). Particularly suitable is lactose and/or maltodextrin. In one embodiment, the composition does not comprise lactose.

The digestible carbohydrate component suitably comprises at least 60 wt % lactose based on total digestible carbohydrate, more suitably at least 75 wt %, even more suitably at least 90 wt % lactose based on total digestible carbohydrate Lipid The composition according to the invention suitably comprises a lipid component, suitably a lipid component suitable for infant nutrition as known in the art. The lipid component of the present composition suitably provides 2.9 to 6.0 g, more suitably 4 to 6 g per 100 kcal of the composition. When in liquid form, the composition suitably comprises 2.1 to 6.5 g lipid per 100 ml, more suitably 3.0 to 4.0 g per 100 ml. Based on dry weight the present infant or follow on formula suitably comprises 12.5 to 40 wt % lipid, more suitably 19 to 30 wt %.

The lipid component typically comprises the essential fatty acids alpha-linolenic acid (ALA), linoleic acid (LA) and suitably long chain polyunsaturated fatty acids (LC-PUFA). The LC-PUFA, LA and/or ALA may be provided as free fatty acids, in triglyceride form, in diglyceride form, in monoglyceride form, in phospholipid form, or as a mixture of one of more of the above. Suitably the present composition contains at least one, suitably at least two lipid sources selected from the group consisting of rape seed oil (such as colza oil, low erucic acid rape seed oil and canola oil), high oleic sunflower oil, high oleic safflower oil, olive oil, marine oils, microbial oils, coconut oil, palm kernel oil and milk fat.

Probiotic

The composition according to the invention comprises a probiotic. In the context of the present invention, the term "probiotic" refers to a strain of probiotic bacteria. Probiotic bacteria are known in the art. Suitably, the probiotic bacteria are not genetically modified.

Suitable probiotic bacteria include bacteria of the genus *Bifidobacteria* (e.g. *B. breve*, *B. longum*, *B. infantis*, *B. bifidum*), *Lactobacillus* (e.g. *L. Acidophilus*, *L. paracasei*, *L. johnsonii*, *L. plantarum*, *L. reuteri*, *L. rhamnosus*, *L. casei*, *L. lactis*), and *Streptococcus* (e.g. *S. thermophilus*). *B. breve* and *B. longum* are especially suitable probiotics.

Most suitably, the probiotic comprises a strain of *B. breve*. The *B. breve* suitably has at least 95% identity of the 16 S rRNA sequence when compared to the type strain of *B. breve* ATCC 15700, more suitably at least 97% identity (Stackebrandt & Goebel, 1994, *Int. J. Syst. Bacteriol.* 44:846-849). Suitable *B. breve* strains may be isolated from the faeces of healthy human milk-fed infants. Typically, these are commercially available from producers of lactic acid bacteria, but they can also be directly isolated from faeces, identified, characterised and produced. According to one embodiment, the present composition contains a *B. breve* selected from the group consisting of *B. breve* Bb-03 (Rhodia/Danisco), *B. breve* M-16V (Morinaga), *B. breve* R0070 (Institute Rosell, Lallemand), *B. breve* BR03 (Probiotical), *B. breve* BR92) (Cell Biotech), DSM 20091, LMG 11613, YIT4065, FERM BP-6223 and CNCM I-2219. Most suitably, the *B. breve* is selected from the group consisting of *B. breve* M-16V and *B. breve* CNCM I-2219, most suitably *B. breve* M-16V. *B. breve* I-2219 was published in WO 2004/093899 and was deposited at the Collection Nationale de Cultures de Microorganisms, Institute Pasteur, Paris, France on 31 May 1999 by Compagnie Gervais Danone. *B. breve* M-16V was deposited as BCCM/LMG23729 and is commercially available from Morinaga Milk Industry Co., Ltd.

The combination of a prebiotic and a probiotic is also referred to as a "synbiotic".

The probiotic may be present in the composition at any suitable concentration, suitably in a therapeutically effective amount or "amount effective for treating" in the context of the invention. Suitably, the probiotic is included in the present composition in an amount of $10^2$-$10^{13}$ cfu per g dry weight of the composition, suitably $10^5$-$10^{12}$ cfu/g, most suitably $10^7$-$10^{10}$ cfu/g.

Application

The composition according to the invention is for inducing oral tolerance and/or treating, preventing and/or reducing the risk occurrence of allergy in a subject. The allergy may be cow's milk protein allergy, suitably allergy to whey protein. (Prophylactic) treatment of allergy preferably involves reducing the (acute) symptoms associated with ingesting an allergen, in particular wherein the allergen is cow's milk protein. Suitably, the (acute) symptoms are reduced when the allergen is ingested again. The allergen is suitably cow's milk protein. In the context of the present invention the term "treatment" is understood to mean a therapeutic treatment of a human or animal patient, suitably humans, in particular infants, in terms of partially or completely curing the allergy and/or to alleviate or ameliorate symptoms of the allergy. Suitably, the treatment is an oral immuno-therapy. In the context of the invention, "prevention" may also be referred to as "reducing the risk or occurrence of", and is understood to mean a prophylactic treatment of a human or animal patient, suitably a human, in particular an infant.

The composition according to the invention can be used as a nutritional composition, nutritional therapy, nutritional support, as a medical food, as a food for special medical purposes or as a nutritional supplement. The present composition is suitably an enteral composition. The composition is administered to, or intended to be administered to, a subject in need thereof, in particular to children and infants, including toddlers, suitably children up to 6 years of age, suitably infants typically with an age of 0-36 month, more suitably 0-12 months of age, most suitably 0-6 months of age. Thus, in some embodiments, the present composition is an infant formula, follow-on formula or growing-up milk, most suitably it is an infant formula.

In a particular embodiment, the composition is for administration to subjects, in particular infants, at risk of developing allergy or suffering from allergy, especially cow's milk protein allergy. Infants that are known to be at risk of developing allergy include infants born from at least one parent suffers from, or has suffered from, atopic disorders (e.g. eczema) and/or allergy, most in particular from CMA.

The present composition is suitably administered in a daily dose of 0.01 mg-1 g beta-lactoglobulin-derived peptides, more suitably 0.1-100 mg, even more suitably 0.5-5 mg, most suitably 1-2.5 mg.

In a further aspect, the present invention further relates to a kit-of-parts comprising or consisting of the following two or three different containers and instructions for use: A first container comprising infant nutrition, a second container comprising a beta-lactoglobulin-derived peptide as defined hereinabove and optionally a third container comprising a probiotic as defined hereinabove. Alternatively, the probiotic can be comprised in the first container.

The infant nutrition is suitably an infant formula, follow-on formula or growing-up milk as known in the art. Most suitably, the infant nutrition is specifically targeted for allergic infants and/or infants at risk of developing allergy, in particular wherein the allergy is CMA. Such allergic formulae are known in the art. The infant nutrition may also be referred to as the composition according to the invention as defined hereinabove, albeit without comprising a beta-lactoglobulin-derived peptide and optionally without comprising a probiotic.

The infant nutrition may or may not comprise the probiotic as defined above. In case the infant nutrition does not contain the probiotic, the kit of parts comprises a third container comprising the probiotic. The third container is typically in the form of a sachet or stickpack and suitably comprises a powder consisting of the probiotic and a acceptable carrier, typically lactose. In case the infant nutrition contains the probiotic, the kit may be limited to the first and second container. The second container is typically in sachet or stickpack and suitably comprises a powder consisting of a beta-lactoglobulin-derived peptide and a acceptable carrier, typically lactose. The instructions for use conveniently instruct the user to combine the contents of the two or three containers in the appropriate format and reconstitute the resulting mixture with a liquid, typically water, to obtain a ready-to-use liquid composition.

EXAMPLES

Example 1

Figure 1:
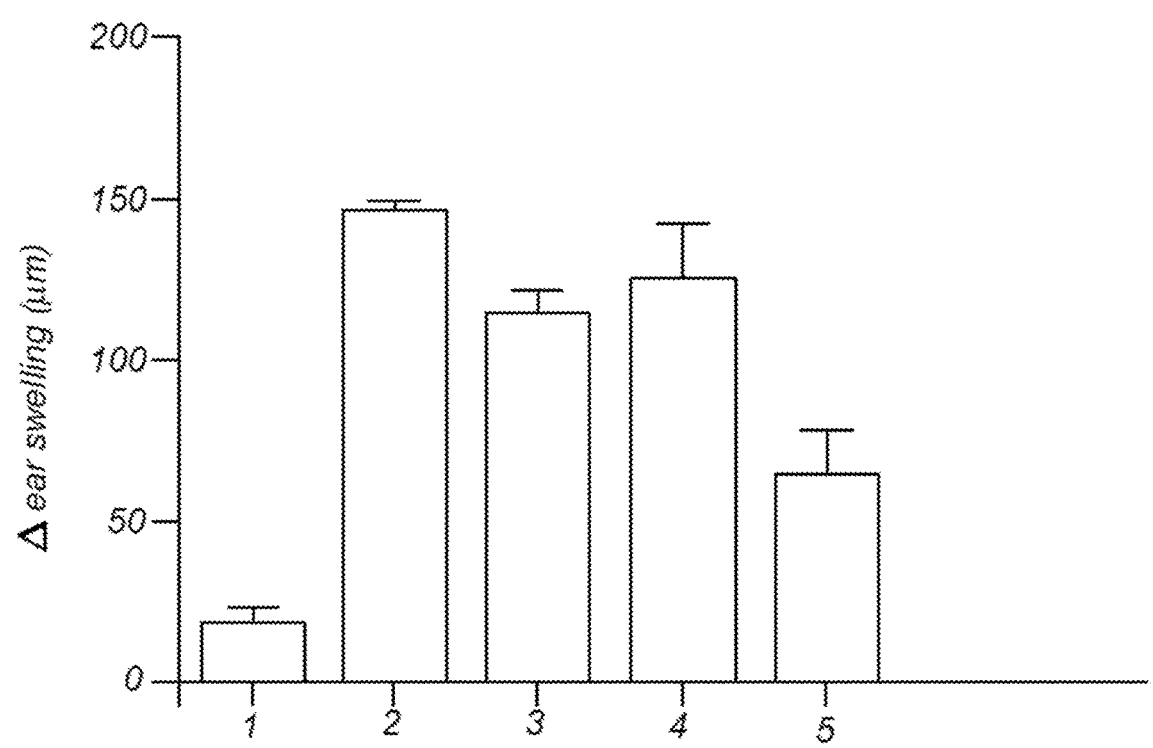
FIG. 1 shows the skin response (ear swelling) results of example 1. The tested groups are: 1=negative control; 2=positive control; 3=peptide-diet group; 4=synbiotics-diet group; 5=peptide+synbiotics-diet group.

Material and Methods
Peptides:

18-amino acid (AA)-long peptides from beta-lactoglobulin were synthetically produced by JPT Peptide Technologies (Berlin, Germany). The synthetic peptides contained a 12-AA-long overlap and their sequence was spanning the B variant of beta-lactoglobulin. The four peptides were previously screened in an assay with human T cell lines by Meulenbroek et al. (Pediatr. Allergy Immunol. 2013:7:656-664) and were selected based on their T cell reactivity for further testing in animal models. Prior to the animal experiment peptides were dissolved in PBS and a mixture of all four peptides was prepared in which each peptide was at a concentration of 0.08 mg/ml ("PepMix"). Peptide sequences are given in Table 1.

TABLE 1

Peptide sequences

| | Peptide | Sequence |
|---|---|---|
| 1 (18 AA) | SEQ ID No. 2 | QKVAGTWYSLANIAASDIS |
| 2 (18 AA) | SEQ ID No. 3 | WYSLANIAASDISLLDAQS |
| 3 (18 AA) | SEQ ID No. 4 | AASDISLLDAQSAPLRVY |
| 4 (18 AA) | SEQ ID No. 5 | LLDAQSAPLRVYVEELKP |

Diets:

Semipurified cow's milk protein-free standard mouse chow was composed based on AIN-93G recipe (control diet) and supplemented with synbiotics (synbiotic diet) (Research Diet Services, Wijk bij Duurstede, The Netherlands). The synbiotic supplementation consisted of 1 wt % of non-digestible short-chain (sc-) and long-chain (lc-) fructo-oligosaccharides (FOS) (Raftilose P95 (Orafti) and Raftiline HP, respectively) in a ratio scFOS/lcFOS=9:1 and 2 wt % $2\times10^9$ CFU/g Bifidobacterium breve M-16V (Morinaga Milk Industry Co., Ltd, Tokyo, Japan). The synbiotic components were mixed through the diet and the mixture was pressed into pellets. Diets were stored at −4° C. prior to use.

Animals:

Three-week-old pathogen-free female C3H/HeOuJ mice were purchased from Charles River Laboratories (Sulzfeld, Germany) and were maintained on a cow's milk protein-free standard mouse chow (AIN-93G soy, Research Diet Services). Mice were housed in the animal facility at Utrecht University. Animal care and use was in accordance with the guidelines of the Dutch Committee of Animal Experiments.

Study Protocol:

In order to investigate the tolerogenic properties of the synthetic peptides in combination with the synbiotic diet, a murine model for cow's milk allergy was used as described by Van Esch et al. (Pediatr Allergy Immunol 2011; 22:820-826). Mice were orally exposed (using a blunt needle) to 0.5 ml of the PepMix or phosphate buffered saline (PBS, Lonza, Walkerville, Md., USA) prior to sensitization (daily; from day −7 to day −2). In the same week (from day −9 to day 0) mice were fed the control diet or the synbiotic diet ad libitum. Subsequently, on day 0, 7, 14, 21 and 28, mice were sensitized orally with 20 mg whey protein (DMV International, Veghel, The Netherlands) homogenized in 0.5 ml PBS and mixed with 10 μg cholera toxin (CT; List Biological Laboratories, Inc. California, USA) as an adjuvant. The non-sensitized mice received 10 μg cholera toxin in 0.5 ml PBS only. Table 2 summarizes the five groups tested.

Five days after the last sensitization, mice underwent an intradermal whey challenge (injection in the ear pinnae with 10 μg whey protein in 20 μl PBS) and the acute allergic skin response was recorded. The ear thickness was measured in duplicate before and 1 h after the intradermal challenge using a digital micrometer (Mitutoyo, Veenendaal, The Netherlands). The allergen-specific ear swelling is the difference between the average ear thickness at 1 h and the average basal ear thickness (Δ=ear thickness at 1 h−basal ear thickness) and is expressed in micrometer. The ear swelling due to the local injection is reflected in the "Δ ear swelling" of the non-sensitized mice (Group 1). Next to the ear swelling, clinical symptoms, such as anaphylactic shock, were monitored and scored according to a table as previously described Van Esch et al. (Pediatr Allergy Immunol 2011; 22:820-826).

TABLE 2

Interventions in the different groups

| Group | Pre-treatment | Sensitization | Challenge |
|---|---|---|---|
| 1 negative control | PBS + control diet | PBS + CT | whey |
| 2 positive control | PBS + control diet | whey + CT | whey |
| 3 peptide | PepMix + control diet | whey + CT | whey |
| 4 synbiotics | PBS + synbiotic diet | whey + CT | whey |
| 5 peptide + synbiotics | PepMix + synbiotic diet | whey + CT | whey |

Statistical Analysis:

All statistical analyses were conducted using GraphPad Prism 6.0c software. Data was analysed with one-way ANOVA and post hoc Bonferroni's multiple comparison test. The anaphylactic shock scores were analysed using Kruskal-Wallis test because of the non-parametric nature of the data. All data is presented as mean±SEM of 5-8 animals per group. P<0.05 was considered of statistical significance.

Results

Figure 2:
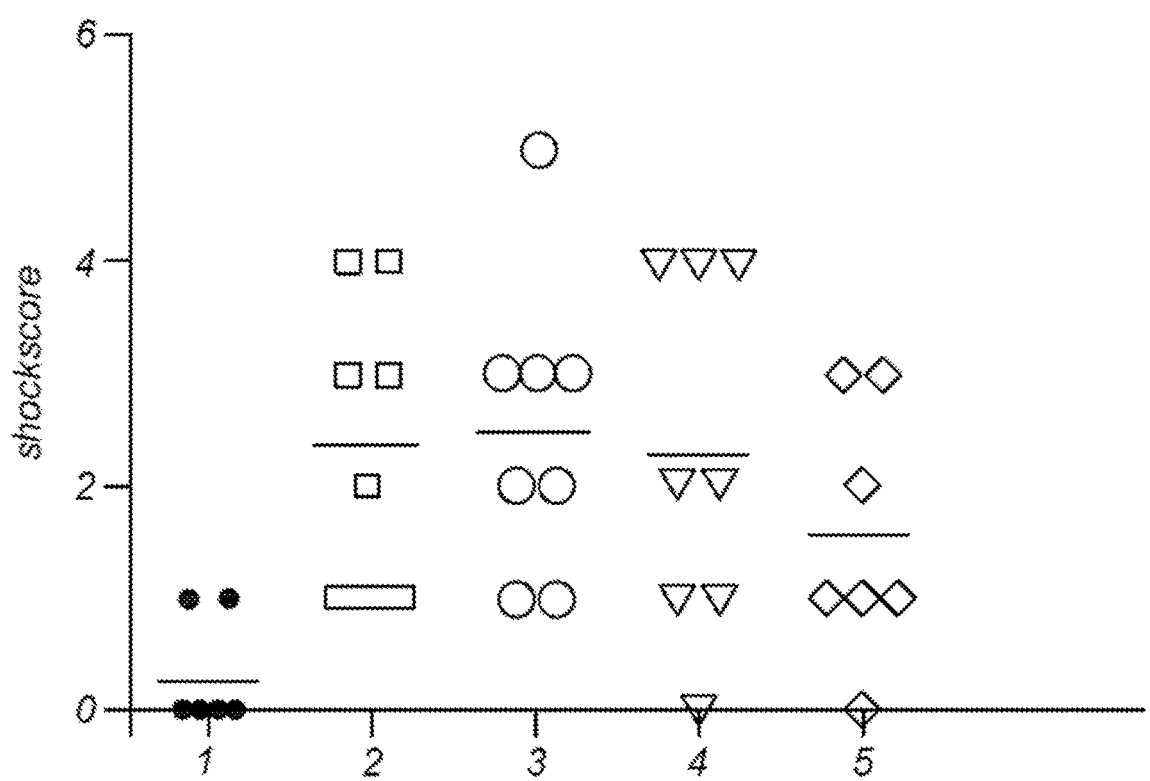
FIG. 2 shows the anaphylactic shock scores of example 1. The tested groups are: 1=negative control; 2=positive control; 3=peptide-diet group; 4=synbiotics-diet group; 5=peptide+synbiotics-diet group.

Skin response results are summarized in FIG. 1 and the results on anaphylactic shock scores in FIG. 2. Sensitized, but untreated animals (Group 2) developed a significantly higher allergic response compared to the non-sensitised ones (Group 1). The allergic response was significantly reduced after pre-exposing the animals to a mixture of tolerogenic peptides combined with a diet containing synbiotics (Group 5). The treatments with the peptide mixture (Group 3) and with synbiotic diet (Group 4) were insufficient to reduce the allergic response when applied alone and only the combined exposure showed to be effective (Group 5). Furthermore, sensitized animals developed significant anaphylactic shock symptoms 20-40 min after the intradermal injection with the allergen. However, only the combined peptides-synbiotics (Group 5) exposure prevented from developing significantly higher anaphylactic shock symptoms when compared to the non-sensitized controls (Group 1). Anaphylactic shock scores were significantly increased in Groups 2, 3 and 4, compared to Group 1.

The above experiment was repeated with the exception that the 1% wt % sc-FOS/lc-FOS was substituted with 1 wt % of sc-galacto-oligosaccharides (GOS) and lc-FOS (Vivinal® GOS and Raftiline HP, respectively) in a ratio scGOS/lcFOS=9:1 for the synbiotic that was fed to the animals. The results from this experiment suggest that pre-exposure of animals with a combination of this synbiotic and the tolerogenic peptide mixture also reduces the allergic response to intradermal whey challenged, as compared to a control.

Example 2

An infant formula for infants at risk of cow's milk protein allergy or for infants allergic to cow's milk protein: Energy density: 0.6-0.77 kcal/ml. Protein is present in the form of free amino acids and the beta-lactoglobulin-derived peptides of the present invention. Per g protein about 100 µg peptide mix as tested in example 1 is present. Further characteristics are given in Table 3.

TABLE 3

Nutritional information

| | per 100 ml* |
|---|---|
| Energy (kJ) | 293 |
| Energy (kcal) | 70 |
| protein (g) | 1.9 (11 en %) |
| carbohydrate (g) | 7.9 (45 en %) |
| lipids (g) | 3.4 (44 en %) |
| LA (g) | 0.6 |
| ALA (mg) | 60 |
| AA (mg) | 12 |
| DHA (mg) | 7 |
| Pepmix of example 1 (µg) | 190 |
| B. breve | $2 \times 10^7$ cfu |

*or per 14.7 g powder to be reconstituted in water to a total of 100 ml

The composition further comprises minerals, vitamins as prescribed for infant formulae, and has an osmolarity of 324 mOsm/L.

Example 3

Materials and Methods
Peptides, Diets, Animals and Treatment Protocol: Same as in Example 1.
Cell Isolation from Tissues:

Lymphocytes were isolated from spleen, mesenteric lymph nodes (MLN) and small intestine lamina propria. Spleens and MLN were crushed through 70 µm cell strainers. Splenocyte suspension was incubated for 5 min. on ice with lysis buffer to remove red blood cells. Both splenocytes and MLN cells were taken up in RPMI 1640 supplemented with 10% FCS and penicillin (100 U/mL)/streptomycin (100 µg/mL). For the isolation of lamina propria cells, the whole small intestine was removed, cleared of Peyer's patches (PP), washed in cold PBS, opened longitudinally, and minced in 0.5 cm fragments. Samples were then washed in Hank's Balanced Salt Solution (HBSS; Invitrogen, Life Technologies, Carlsbad, Calif., USA) supplemented with 15 µM HEPES (Gibco, Life Technologies, Carlsbad, Calif., USA), pH=7.2 followed by 4×15 min incubations with HBSS supplemented with 15 µM HEPES, 5 µM Naz-EDTA, 10% FCS and penicillin (100 U/mL)/streptomycin (100 µg/mL), pH=7.2. The fragments were then washed in RPMI 1640 supplemented with 5% FCS and penicillin (100 U/mL)/streptomycin (100 µg/mL) and incubated 2×45 min with an enzyme solution containing RPMI 1640, 5% FCS, penicillin (100 U/mL)/streptomycin (100 µg/mL) and 0.25 mg/mL Collgenase type VIII (Sigma-Aldrich). In order to collect the small intestine lamina propria cells, fragments were vortexed for 10 s after each incubation and poured over a 70 µm cell strainer. Cell were washed once and used for flow cytometry.

Flow Cytometry Analysis of T Cell Subsets:

Phenotypic characterisation of T cell subsets was performed by means of flow cytometry. Cells were resuspended in PBS/1% BSA and were incubated for 15 min with anti-mouse CD16/CD32 (Mouse BD Fc Block; BD Pharmingen, San Jose, Calif., USA). For determining the $T_h1/T_h2$ subsets, cells were extracellularly stained with CD4-PerCp-Cy5.5, CD69-APC, CXCR3-PE (eBiosciences, San Diego, Calif., USA) and T1ST2-FITC (MD Biosciences, St. Paul, Minn., USA). After staining extracellular markers, cells were stained with a fixable viability dye AlexaFluor780 (eBioscience). Results were collected with BD FACSCanto II flow cytometer (Becton Dickinson, Franklin Lakes, N.J., USA) and were analysed with FlowLogic software (Inivai Technologies, Mentone, VIC, Australia).

Figure 3:
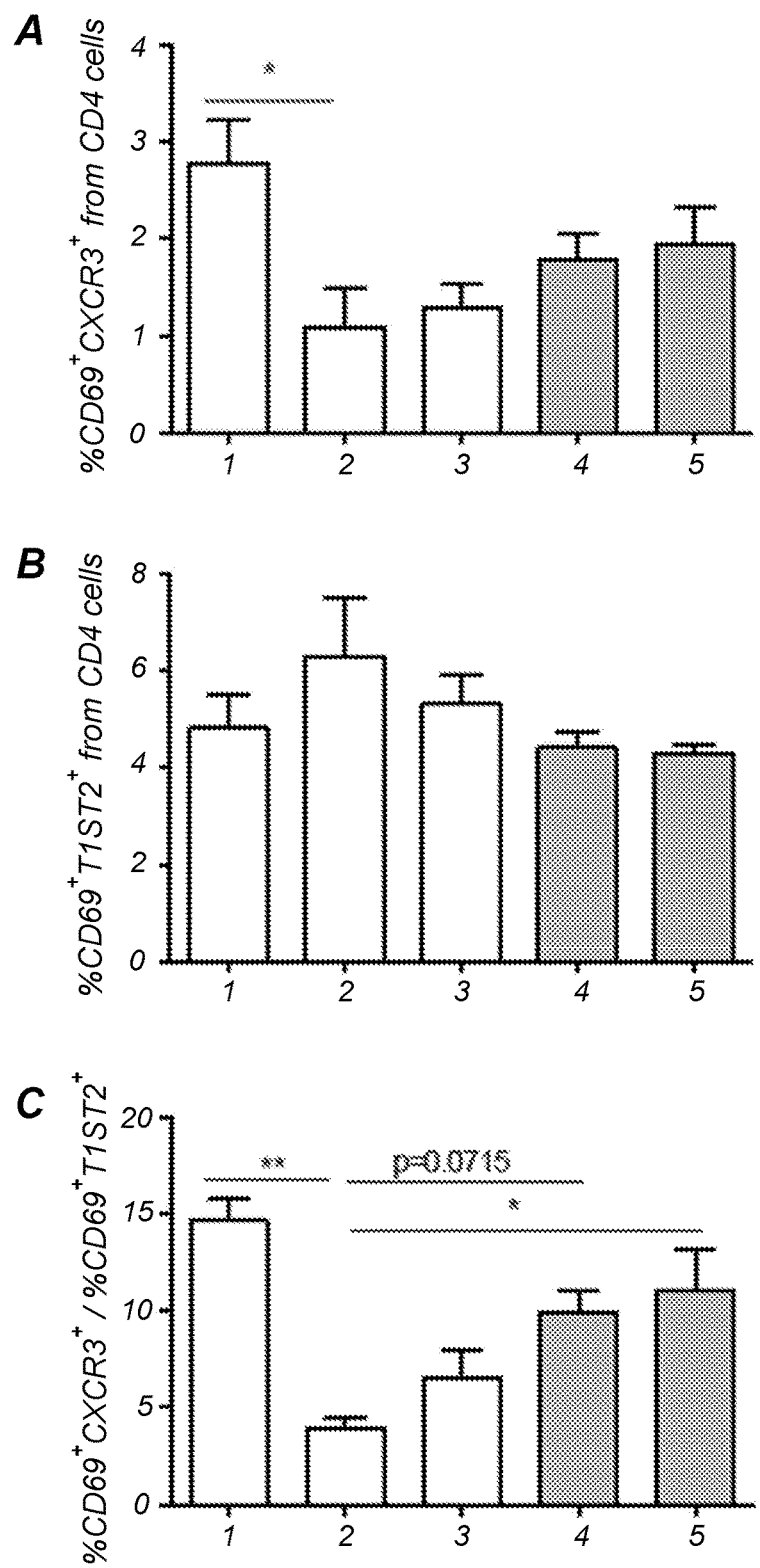
FIG. 3 shows the T cell subset analysis results of example 3. Lymphocytes isolated from the small intestine lamina propria (SI-LP) were analysed by flow cytometry for $T_h1$ and $T_h2$ phenotypes. The tested groups are: 1=negative control; 2=positive control; 3=peptide-diet group; 4=synbiotics-diet group; 5=peptide+synbiotics-diet group. Test groups fed a synbiotics diet are shown with a solid grey bar. For each tested group the percentage of $CD4^+$ cells with an activated $T_h1$ phenotype (Graph A) or with an activated $T_h2$ phenotype (Graph B) are shown, as well as the $T_h1/T_h2$ ratios within an individual $CD4^+$ population (Graph C). Data are presented as the mean±SEM of n=4 in the negative control group and n=6-8 in all other groups. * $p<0.05$, ** $p<0.01$ as analysed with ANOVA followed by Bonferroni post hoc test for selected groups.

Ex Vivo Re-Stimulation Assay and Cytokine Levels:

After sacrifice, spleens were removed and a single cell suspension was obtained. Then splenocytes ($6 \times 10^5$ cells) were cultured either with medium or with 500 µg/mL whey protein at 37° C., 5% $CO_2$. After 5 days of incubation, supernatants were collected and stored at −20° C. until further analysis. Cytokine quantification of IL-5, IL-13, IL-10, IL-17A and IFN-γ was performed by means of a Cytometric Bead Array (CBA) Flex Set assay (BD Biosciences) following manufacturer's instructions. Beads were analysed with BD FACSCanto II flow cytometer and results were obtained in FCAP v. 3.0 software (Becton Dickinson).
Statistical Analysis:

All statistical analyses used GraphPad Prism 6.0c software for Macintosh (GraphPad Software, San Diego, Calif., USA). All data was analysed for normality and equality of variance. One-way ANOVA, followed by a Bonferroni's multiple comparison post hoc test for selected groups (7 pre-selected comparisons) was used when possible. When data was not normally distributed, as in the case of cytokines levels, it was first LOG-transformed and tested again. If LOG transformation did not improve normality, then the non-parametric Kruskal-Wallis test was used, followed by a Dunn's post hoc for selected groups and 7 pre-selected comparisons. All data is presented as mean±SEM of 4-8 animals per group. P<0.05 was considered of statistical significance.
Results In order to investigate the local effects in the intestine, lamina propria lymphocytes from the small intestine (SI-LP) were isolated and analysed by flow cytometry for the different T cell subsets. In line with the paradigm that allergy influences the balance between $T_h1$ and $T_h2$ lymphocytes skewing it toward the $T_h2$ environment (Cox, H E, J Pediatr Gastroenterol Nutr 2008; 47 Suppl 2, S45-48), it was observed that allergic mice showed significantly lower numbers of activated $T_h1$ cells, while activated $T_h2$ cells appeared to increase in number (FIG. 3). As a result, the ratio of activated $T_h1/T_h2$ cells was shifted in favour of $T_h2$ in the allergic control mice (Group 2), while prior feeding with peptides and synbiotics (Group 5) prevented this shift. Feeding mice only the synbiotics-supplemented diet (Group 4) tended to preserve the $T_h1/T_h2$ balance but less pronounced compared to the combination with peptides, suggesting that the synbiotics ensure a favourable milieu during the presentation of the peptides by antigen presenting cells.

Figure 4:
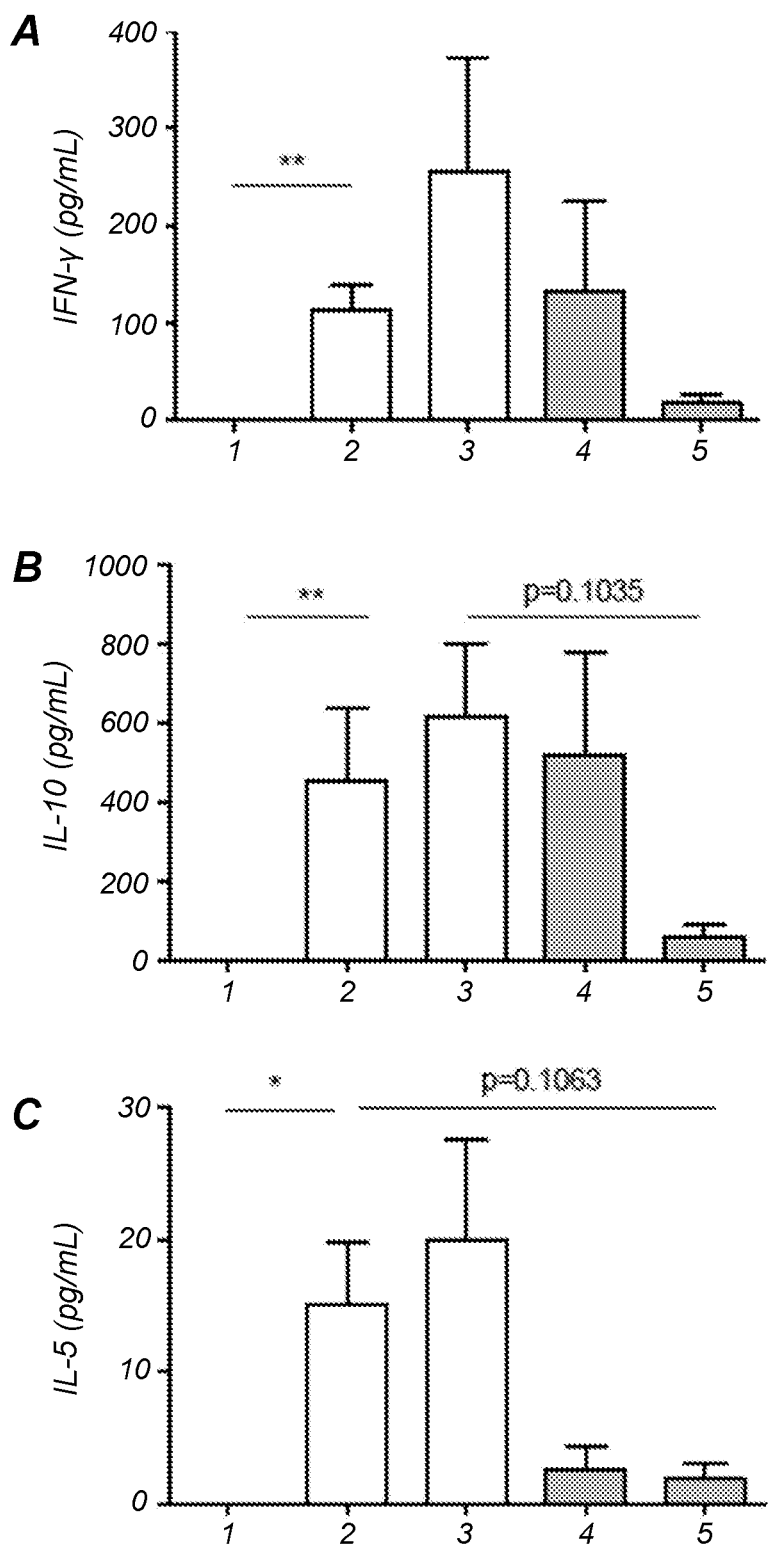
FIG. 4 shows the ex vivo splenocyte cytokine production results of example 3. The tested groups are: 1=negative control; 2=positive control; 3=peptide-diet group; 4=synbiotics-diet group; 5=peptide+synbiotics-diet group. Test groups fed a synbiotics diet are shown with a solid grey bar. The tested cytokines are: IL-13 (Graph A), IL-10 (Graph B), IL-5 (Graph C), IL-17A (Graph D) and IFN-γ (Graph E). Data are presented as the mean±SEM of n=4 in the PBS/CT group and n=6-8 in all other groups. * $p<0.05$, ** $p<0.01$ as analysed with Kruskal-Wallis non-parametric test, followed by Dunn's post hoc test for selected groups.
Figure 4:
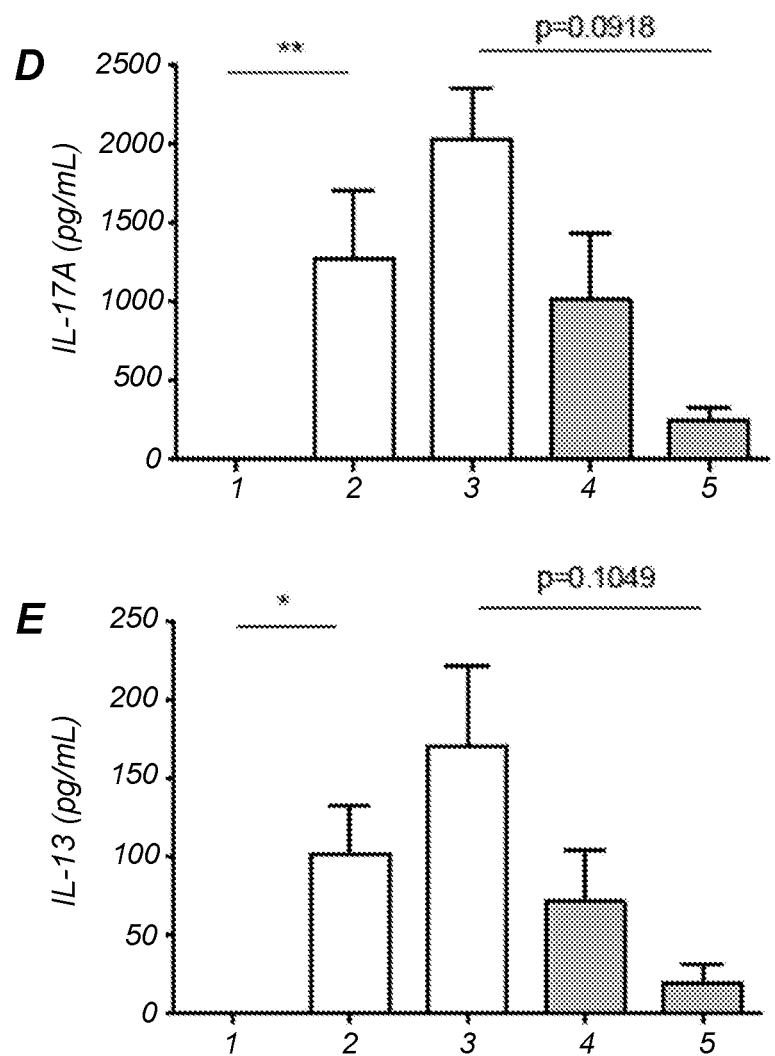

To investigate whether the preventive treatments affect the functionality of cells in the systemic compartment, spleens from the treated groups were collected 18 h after the oral challenge and splenic lymphocytes were stimulated ex vivo with allergen for 5 days in order to determine their capacity to produce cytokines. The results presented in FIG. 4 show that the functionality of splenocytes was affected by pre-exposure to the combination of peptides and synbiotics-enriched diet (Group 5). Functionality was assessed by assaying allergy-related $T_h2$ cytokines (IL-13, IL-5, IL-10) as well as $T_h1$-(IFN-γ) and Th17-assosiated ones (IL-17A). Notably, cells from allergic controls (Group 2) markedly produced all these cytokines; not only the $T_h2$-associated cytokines. However, cells from animals treated with a combination of peptide mixture and synbiotics (Group 5) tended to induce less IL-17A, IL-10 and IL-13, as compared to the peptide mixture alone (Group 3).

These results indicate that combined exposure to peptide mixture and synbiotics reduces allergen-induced cytokine production and prevents unfavourable shift in the $T_h1/T_h2$ balance in the intestinal lamina propria.

Example 4

Materials and Methods
Peptides:
Same as example 1 except that prior to the animal experiment peptides were dissolved in PBS and a mixture of all four peptides was prepared in which each peptide was at a concentration of 0.8 mg/mL ("PepMix")
Animals:
Same as in example 1.
Statistical Analysis:
Statistical analyses were conducted using GraphPad Prism 6.0c software for Macintosh (GraphPad Software, San Diego, Calif., USA). Data was analysed with one-way ANOVA and post hoc Dunnett's multiple comparison test. Data is presented as mean±SEM of 6-8 animals per group. P<0.05 was considered of statistical significance.
Diets:
Semipurified cow's milk protein-free standard mouse chow was composed based on AIN-93G recipe (control diet) and supplemented with 2 wt % 2×10⁹ CFU/g *Bifidobacterium breve* M-16V (Morinaga Milk Industry Co., Ltd, Tokyo, Japan) (probiotic diet). The probiotic component was mixed through the diet and the mixture was pressed into pellets. Diets were stored at −4° C. prior to use.

Study Protocol:
Mice were orally exposed (using a blunt needle) to 0.5 mL of the PepMix or phosphate buffered saline (PBS, Lonza, Walkerville, Md., USA) prior to sensitization (daily; from day −7 to day −2). In the same week (from day −9 to day 0) mice were fed the control diet or the probiotic diet ad libitum. Subsequently, on day 0, 7, 14, 21 and 28, mice were sensitized orally with 20 mg whey protein (DMV International, Veghel, The Netherlands) homogenized in 0.5 mL PBS and mixed with 10 μg cholera toxin (CT; List Biological Laboratories, Inc. California, USA) as an adjuvant. The non-sensitized mice received 10 μg cholera toxin in 0.5 mL PBS only. Table 3 summarizes the five groups tested.

Five days after the last sensitization, mice underwent an intradermal whey challenge (injection in the ear pinnae with 10 μg whey protein in 20 μl PBS) and the acute allergic skin response was recorded, as described in example 1.

TABLE 3

Interventions in the different groups

| Group | Pre-treatment | Sensitization | Challenge |
|---|---|---|---|
| 1 negative control | PBS + control diet | PBS + CT | whey |
| 2 positive control | PBS + control diet | whey + CT | whey |
| 3 peptide | PepMix + control diet | whey + CT | whey |
| 4 probiotics | PBS + probiotic diet | whey + CT | whey |
| 5 peptide + probiotics | PepMix + probiotic diet | whey + CT | whey |

Figure 5:
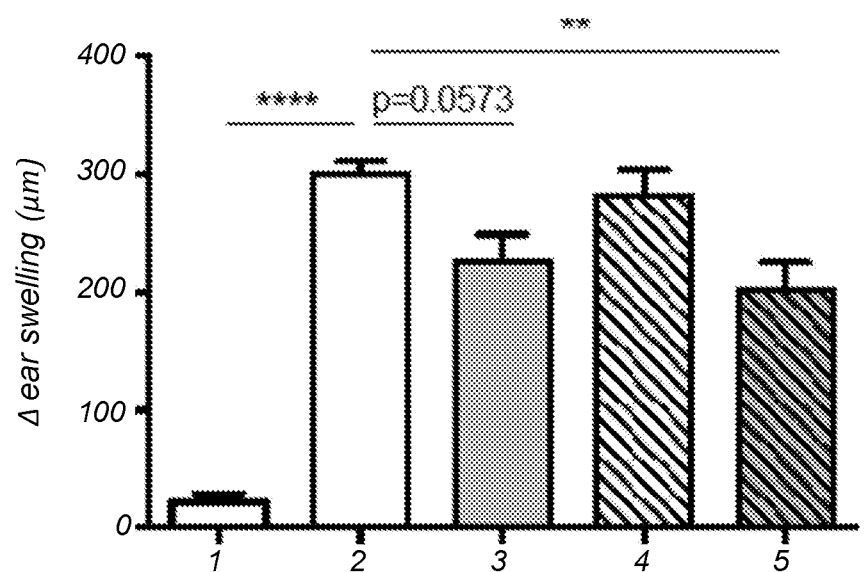
FIG. 5 shows the skin response (ear swelling) results of example 4. The tested groups are: 1=negative control; 2=positive control; 3=peptide-diet group (solid grey bar); 4=probiotics-diet group (diagnonally striped bar); 5=peptide+probiotics-diet group (diagnonally striped bar and a grey background). Data are presented as the mean±SEM of n=6-8 in all other groups. ** p<0.0001,  p<0.01 as analysed with ANOVA followed by Dunnette's post hoc test for selected groups.

Results
Skin response results are summarized in FIG. 5. Sensitized, but untreated animals (Group 2) developed a significantly higher allergic response compared to the non-sensitised ones (Group 1). The treatment with probiotic alone (Group 4) did not significantly reduce the allergic response. However, the allergic response was significantly reduced after pre-exposing the animals to a mixture of tolerogenic peptides alone (Group 3) and this reduction was more pronounced when the tolerogenic peptides were combined with a diet containing probiotics (Group 5).

The invention claimed is:

1. A method for inducing oral tolerance, and/or treating, or reducing the risk of allergy in a subject, comprising administering to the subject a composition comprising:
   (i) $10^2$-$10^{13}$ cfu, per g dry weight of the composition, of a probiotic *Bifidobacteria breve*, and
   (ii) 2 to 10 distinct beta-lactoglobulin-derived peptides comprising an amino acid sequence consisting of 14 to 25 consecutive amino acids from amino acid nos. 13 to 48 of the beta-lactoglobulin protein represented by SEQ ID No. 1.

2. The method according to claim 1, wherein the beta-lactoglobulin-derived peptide consists of an amino acid sequence selected from the group consisting of SEQ ID Nos. 2-5, optionally coupled to 1-6 further amino acids at its C- and/or N-terminus.

3. The method according to claim 1, wherein the composition further comprises a prebiotic.

4. The method according to claim 3, wherein the prebiotic is selected from the group consisting of fructo-oligosaccharide, non-digestible dextrin, galacto-oligosaccharide, xylo-oligosaccharide, arabino-oligosaccharide, arabino-galacto-oligosaccharide, gluco-oligosaccharide, glucomanno-oligosaccharide, galactomanno-oligosaccharide, mannan-oligosaccharide, chito-oligosaccharide, uronic acid oligosaccharide, sialyl-oligosaccharide and fuco-oligosaccharide.

5. The method according to claim 3, wherein the prebiotic comprises a galacto-oligosaccharide and/or a fructo-oligosaccharide.

6. The method according to claim 4, wherein the prebiotic comprises a mixture of a short-chain oligosaccharide having an average degree of polymerisation of 2-8 and a long-chain oligosaccharide having an average degree of polymerisation of 10-60.

7. The method according to claim 1, comprising a further probiotic strain selected from the group consisting of *Lactobacillus acidophilus, Lactobacillus paracasei, Lactobacillus johnsonii, Lactobacillus plantarum, Lactobacillus reuteri, Lactobacillus rhamnosus, Lactobacillus casei, Lactobacillus lactis* and *Streptococcus* thermophiles.

8. The method according to claim 1, wherein the comprises *Bifidobacterium breve* and *Bifidobacterium longum*.

9. The method according to claim 1, wherein the composition comprises 10-50 μg beta-lactoglobulin-derived peptides per gram total protein.

10. The method according to claim 1, wherein the allergy is cow's milk protein allergy.

11. The method according to claim 1, wherein the *Bifidobacterium breve* is the sole probiotic.

12. The method according to claim 3, wherein the composition comprises 0.5-2 wt % of the prebiotic.

* * * * *